US008388894B2

(12) United States Patent  (10) Patent No.: US 8,388,894 B2
Colantonio et al.  (45) Date of Patent: Mar. 5, 2013

(54) APPARATUS AND METHOD FOR STERILIZING A TUBULAR MEDICAL LINE PORT

(75) Inventors: Anthony J. Colantonio, Meadville, PA (US); Menno D. Jager, Meadville, PA (US)

(73) Assignee: PSI Medical Catheter Care, LLC, Erie, PA (US)

( * ) Notice: Subject to any disclaimer, the term of this patent is extended or adjusted under 35 U.S.C. 154(b) by 673 days.

(21) Appl. No.: 12/590,339

(22) Filed: Nov. 6, 2009

(65) Prior Publication Data
US 2010/0050351 A1  Mar. 4, 2010

Related U.S. Application Data

(63) Continuation-in-part of application No. 12/077,881, filed on Mar. 20, 2008, now abandoned.

(51) Int. Cl.
*A61L 2/28* (2006.01)
*A61L 2/00* (2006.01)
(52) U.S. Cl. .................... 422/119; 422/294; 604/905
(58) Field of Classification Search .................. 422/119, 422/294; 604/905
See application file for complete search history.

(56) References Cited

U.S. PATENT DOCUMENTS

| 5,554,135 A * | 9/1996 | Menyhay ................. 604/256 |
| 2007/0112333 A1* | 5/2007 | Hoang et al. .............. 604/533 |
| 2010/0172794 A1* | 7/2010 | Ferlic et al. ................ 422/28 |

* cited by examiner

*Primary Examiner* — Kevin Joyner
(74) *Attorney, Agent, or Firm* — Carothers and Carothers (57) ABSTRACT

An apparatus for sterilizing a tubular medical line port, having a cap with an open distal end and a cavity therein which is dimensioned to receive an outer scrubbing member and the medical line port. Outer disinfected-impregnated scrubbing member is coaxially received in the cavity and has a socket therein dimensioned for engaging exterior side surfaces of the tubular medical line port when inserted into the socket for thereby scrubbing exterior surfaces of the port with the scrubbing member by rotating the cap. The outer scrubbing member is axially displacable downwardly in the cavity by insertion of the medical line port therein from an upper position prior to use to a lower position where it is retained to thereby indicate that the apparatus has been used and should not therefore be reused. A reuse prevention insert is also provided in the cavity of the cap and is displacable with the outer scrubbing member from the upper position prior to use to the lower position during and after use. This insert is provided with inwardly protruding teeth that are biased for inward compression and thereby prevent re-access of a medical line port into the socket of the scrubbing member after removal of the medical line port.

11 Claims, 11 Drawing Sheets

APPARATUS AND METHOD FOR STERILIZING A TUBULAR MEDICAL LINE PORT

CROSS REFERENCE

This application is a continuation-in-part of U.S. patent application Ser. No. 12/077,881, filed Mar. 20, 2008, now abandoned.

FIELD OF THE INVENTION

The present invention relates to the field of medical liquid administration, and more particularly, to an apparatus and method for applying antiseptic to the female end of a medical infusion apparatus.

BACKGROUND OF THE INVENTION

Improvements in patient safety have been among the primary concerns of many efforts in today's healthcare industry. Healthcare associated infections remain a major area of focus for these efforts. The Center for Disease Control and Prevention cites healthcare associated infections in the top ten leading causes of death in the United States. Annually, healthcare associated infections account for an estimated 1.7 million infections in hospitals, 99,000 associated deaths, and 4.5 to 5.7 billion dollars in added patient care costs.

The reduction of healthcare associated infections depends upon awareness and adherence to aseptic technique when handling medical equipment that comes into direct contact with a patient. Medical equipment is constantly threatened by exposure to surrounding contaminated surfaces. These surfaces contain microorganisms (bacteria) which can easily adhere to the surface of medical equipment. Once contaminated, the medical equipment becomes a danger to the patient and can serve as a silent killer.

Healthcare institutions use millions of intravenous catheters each year. These catheters are at risk of contamination by a variety of mechanisms. One such mechanism relates to the contamination of the exposed ports of intravenous (IV) administration sets. This particular problem arises when an intravenous infusion line is temporarily disconnected from a patient (a process which can occur multiple times per day for an individual patient). During the time that the infusion line is disconnected from the patient, the exposed port of the intravenous line may contact potential contaminants. These contaminants could then lead to infection within a patient's bloodstream.

The critical event in the aforementioned circumstance is the failure to retain the sterility of the intravenous port(s) and failure to adequately disinfect the port in the instance of inadvertent contamination during the time of disconnect from infusion tubing. This risk is, in part, an unanticipated outcome of the somewhat recent implementation of needle-less intravenous systems.

Currently, many practitioners are not actively considering the risk of contamination and are not taking steps to secure the sterility of exposed ports. When efforts are made to maintain the sterility of exposed ports, these efforts are both cumbersome (and therefore at times skipped over), or they fail due to technical shortcomings.

Safe practice recommendations include the use of aseptic technique when handling medical infusion lines. The current aseptic technique, as pertains specifically to intravenous catheters, includes sterilizing the exposed ports used for intermittent infusions with alcohol prep pads between uses. Disinfecting the surfaces of medical equipment with alcohol is a well accepted and established practice. Evidence exists supporting the use of a one minute alcohol exposure as an adequate disinfecting technique.

Current practice often utilizes alcohol cloth swabs to accomplish the task of disinfecting the surface of medical equipment, including intravenous tubing ports. This method has faults limiting its use. The exposure of the port to the cloth swab of alcohol is often performed in variable fashion. With variable techniques and inadequate exposure times to the disinfectant, successful sterilization is unlikely over the entirety of the surface area on female ports. In addition, the current standard disinfecting system of using an alcohol pad exposes the port, to the skin of the practitioner during and immediately after the disinfecting process. Lastly, the alcohol prep pads containing the cloth swabs may not be immediately available for use at the time of greatest need.

The port protection system disclosed in this invention description includes a means to temporarily and safely cover and apply antiseptic to the female end of a medical infusion apparatus. In this way, the device and associated method described will adequately provide a means to maintain the sterility of an indwelling intravenous administration set (or other medical infusion lines) that has been disconnected from a patient until it is ready to be reattached for future use.

SUMMARY OF THE INVENTION

The apparatus of the present invention for sterilizing a tubular medical line port, such as a needleless IV port, is comprised of a cap having an open cavity on a distal end which is dimensioned to receive the medical line port therein for sterilization. The cap provides a handle on the proximal end for grasping and manipulating the cap.

An outer disinfectant-impregnated member is coaxially received in the cavity and dimensioned for engaging exterior surfaces of a tubular port when inserted into the cavity to be disinfected. The handle end of the cap is rotated to accordingly scrub the exterior surfaces of the tubular port for sterilization.

The apparatus of the present invention is so constructed that the outer scrubbing member is axially displacable downwardly in the cavity of the cap by insertion of a medical line port into the member. The outer scrubbing member is thus displacable from an upper position prior to use to a lower position in the cavity where it is retained to thereby indicate to the personnel using the apparatus that it has been used and should not therefore be reused. An indicating surface is provided in the cavity which is exposed only after downward displacement of the outer scrubbing member below the indicating surface to indicate the apparatus has been used.

A compressible sponge which is saturated with disinfectant fluid is positioned under the outer scrubbing member whereby the sponge is compressed to expel the disinfecting fluid therefrom to the outer scrubbing member when it is displaced to the lower position.

An annular inwardly extending protrusion is provided in the cavity and positioned for retaining the outer scrubbing element in the aforesaid lower position by engaging the upper surface of the outer scrubbing member after it is displaced downwardly beyond the protrusion.

The outer scrubbing member may also include female threads to threadably receive and mate male threads on the medical line port.

The cavity of the cap is provided with a frusto-conical wall which tapers inwardly from top to bottom whereby the outer scrubbing member is squeezed radially inward upon displacement to the aforesaid lower position for pressure scrubbing engagement with the medical line port inserted therein.

In one embodiment, a reuse prevention insert is provided in the cavity of the cap and is displacable with the outer scrubbing member. The insert has inwardly protruding and inwardly biased teeth which prevent re-access of a medical line port into the cavity after removal under the biased inward engagement of the teeth of the reuse prevention insert. The reuse prevention insert includes multiple legs which are annularly disposed on and about the frusto-conical wall of the cavity and these legs are generally aligned with the central axis of the wall. The inwardly protruding teeth protrude from upper ends of the leg. Accordingly, when the legs are displaced downwardly, together with the outer scrubbing member, the upper end of the legs, together with the inwardly protruding teeth are compressed inwardly against the inserted medical line port. When the medical line port is removed, the inwardly protruding teeth are under bias and are displaced radially inward thereby partially closing off the upper opening or mouth of the outer scrubbing member to prevent access of another medical line port. To provide this bias for the inwardly protruding teeth, the frusto-conical wall of the cap is comprised of a flexible material. The inwardly protruding teeth may also in and of themselves be comprised of a compressible plastic material.

The outer scrubbing member may also include an inner scrubbing member which extends axially upward from the bottom of the scrubbing element to scrub interior surfaces of the inserted tubular medical line port.

BRIEF DESCRIPTION OF THE DRAWINGS

Other objects and advantages appear hereinafter in the following description and claims, the accompanying drawings show, for the purpose of exemplification, without limiting the scope of the invention or the appended claims, certain practical embodiments of the present invention wherein:

DETAILED DESCRIPTION OF THE PREFERRED EMBODIMENTS

Figure 1:
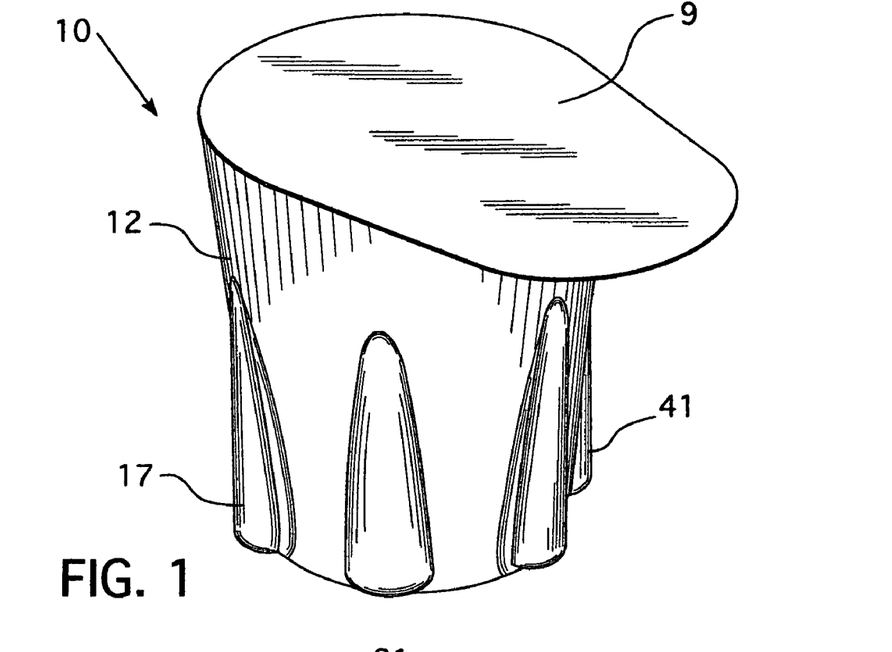
FIG. 1 is a perspective view illustrating a first embodiment of the apparatus of the present invention for sterilizing a female tubular medical line port and shown with a peel-off cover seal over the mouth.
Figure 2:
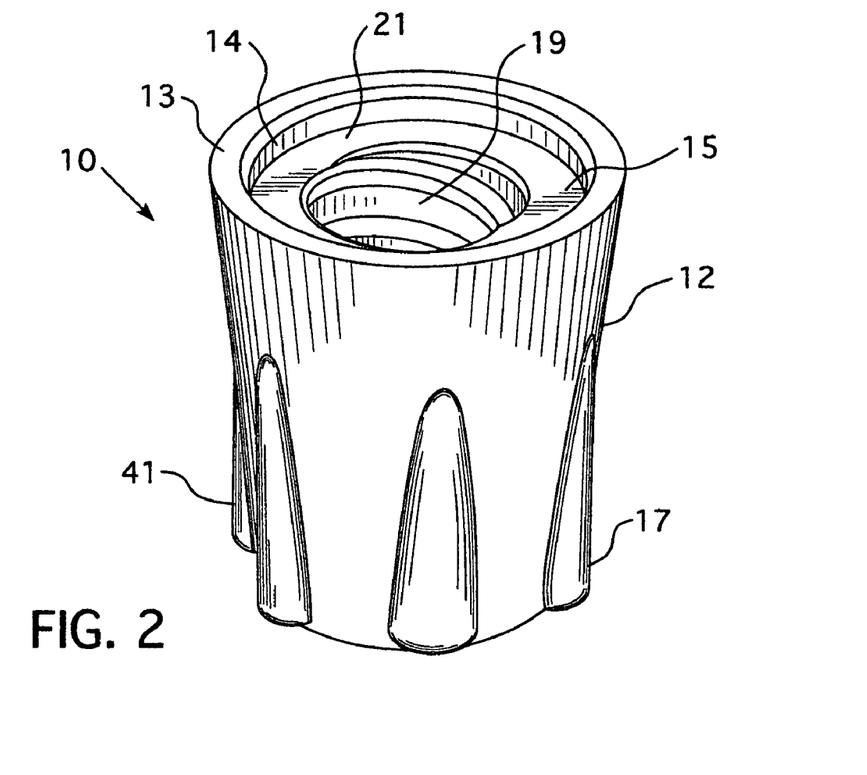
FIG. 2 is a perspective view of the apparatus shown in FIG. 1 with the cover seal removed.
Figure 3:
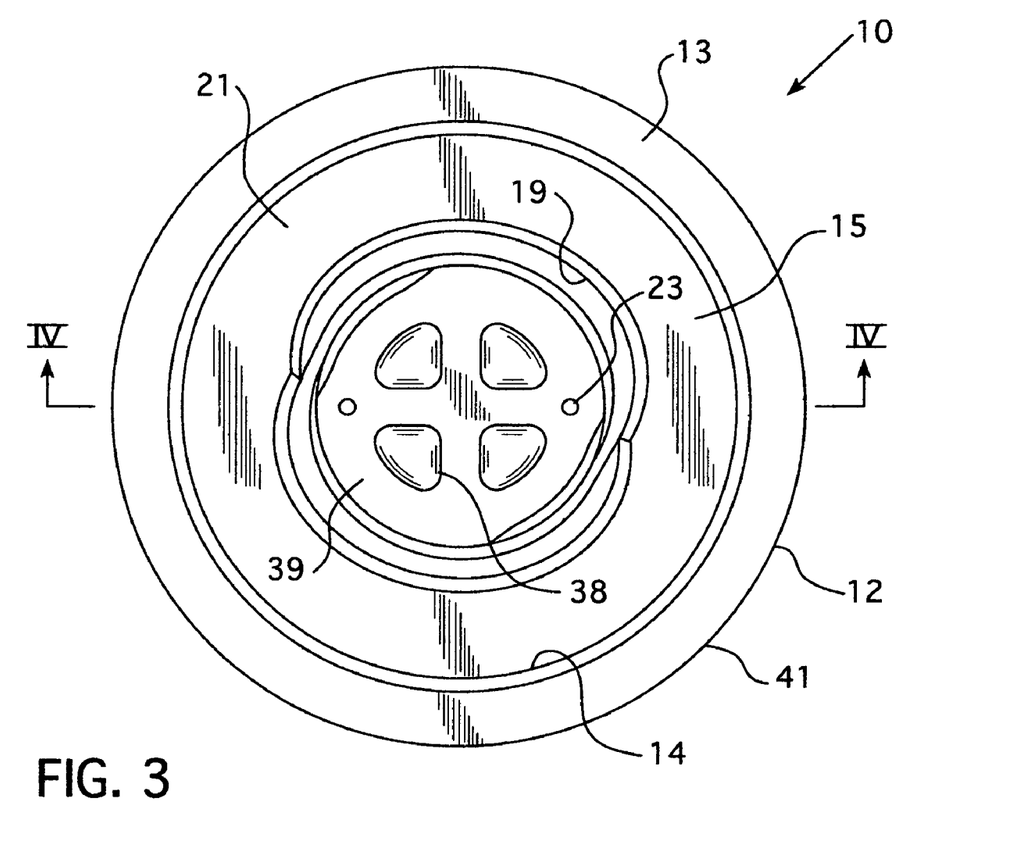
FIG. 3 is a top view of the apparatus shown in FIG. 2.
Figure 4:
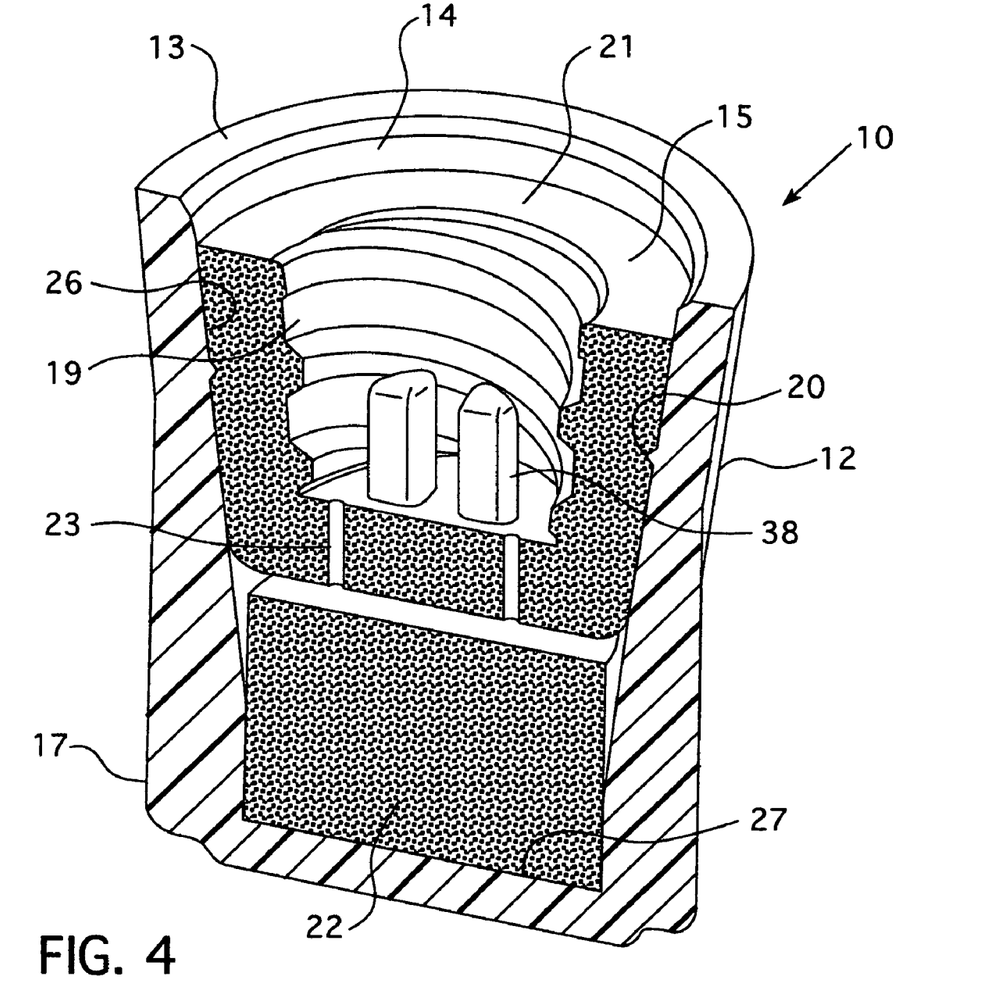
FIG. 4 is a perspective view in vertical mid cross section of the apparatus shown in FIG. 3 as seen along section line IV-IV.
Figure 5:
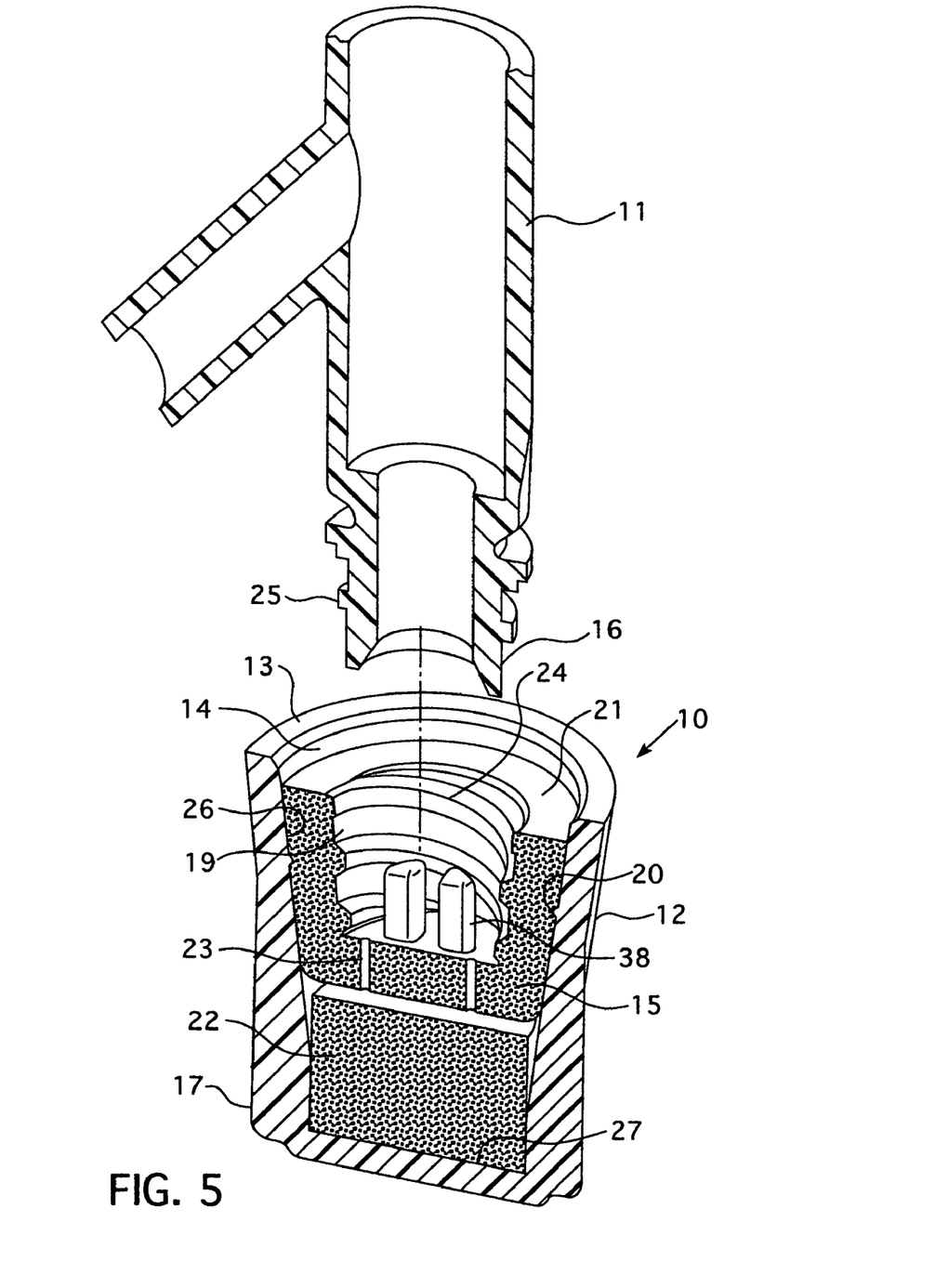
FIG. 5 is a perspective view shown in the same vertical mid cross section as FIG. 4, together with a female medical line port also shown in vertical mid cross section and shown just prior to insertion into the apparatus of the present invention.
Figure 6:
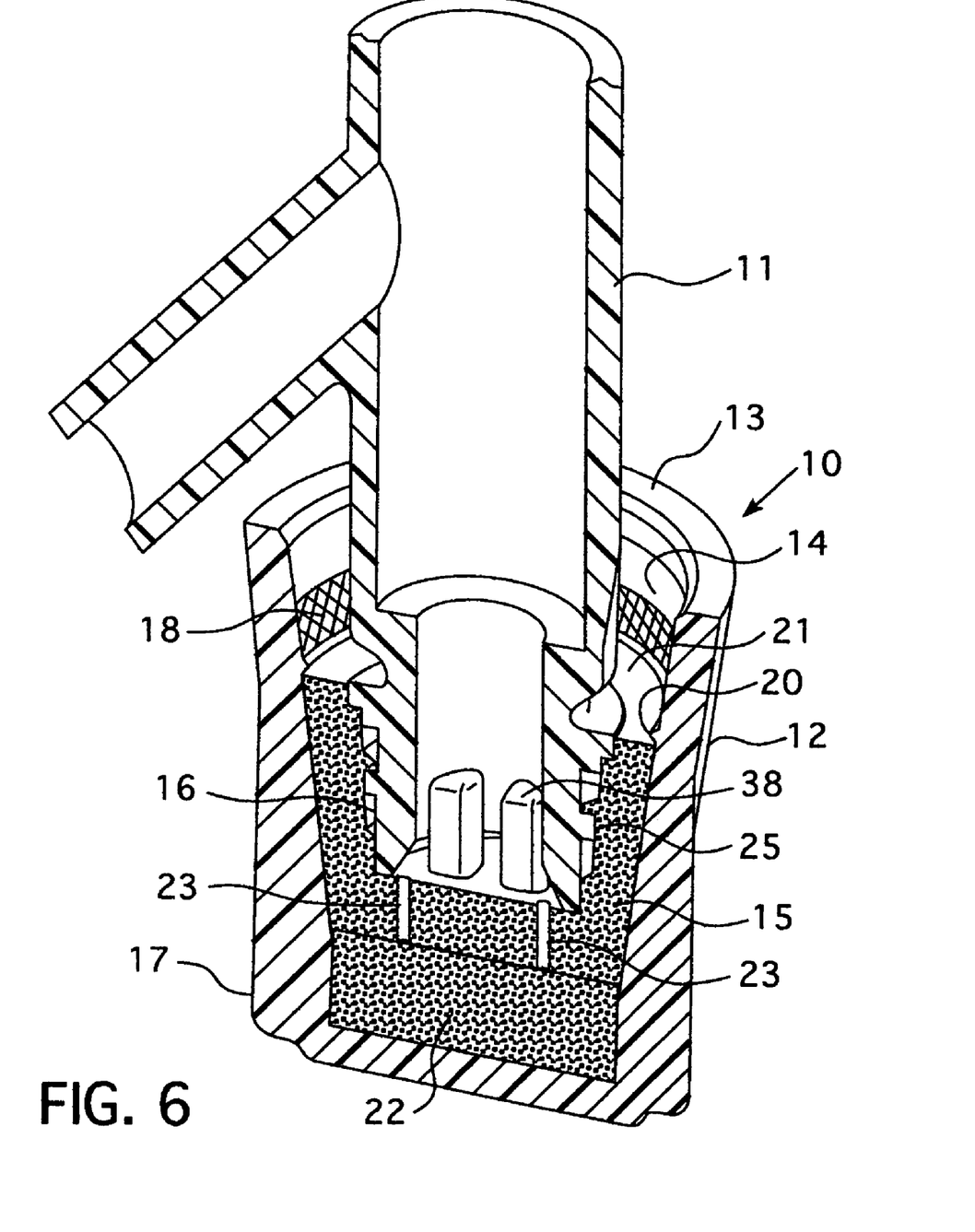
FIG. 6 is a perspective view in vertical mid cross section of the apparatus combination shown in FIG. 5 with the female medical line port illustrated as being fully inserted into the apparatus of the present invention for sterilization scrubbing thereon.
Figure 7:
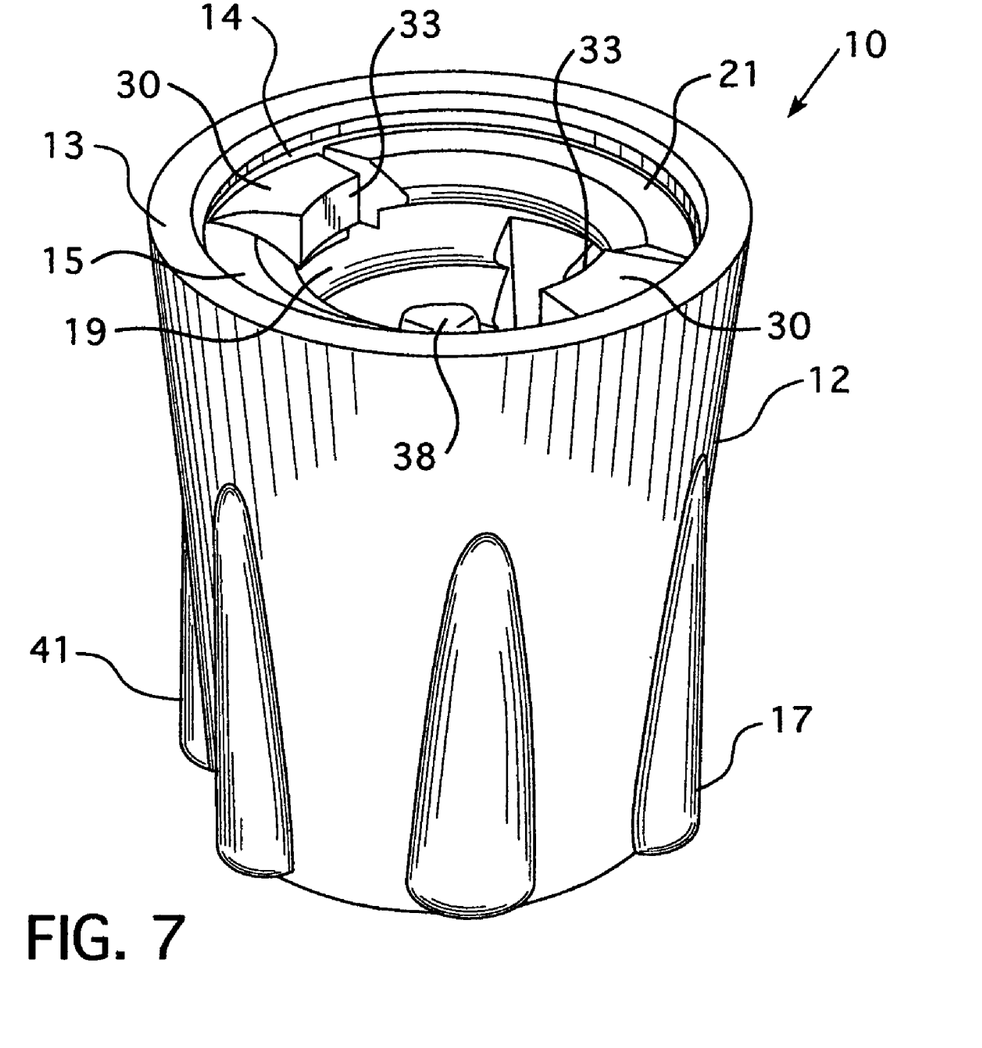
FIG. 7 is a perspective view of a second embodiment of the apparatus of the present invention incorporating a reuse prevention insert.
Figure 8:
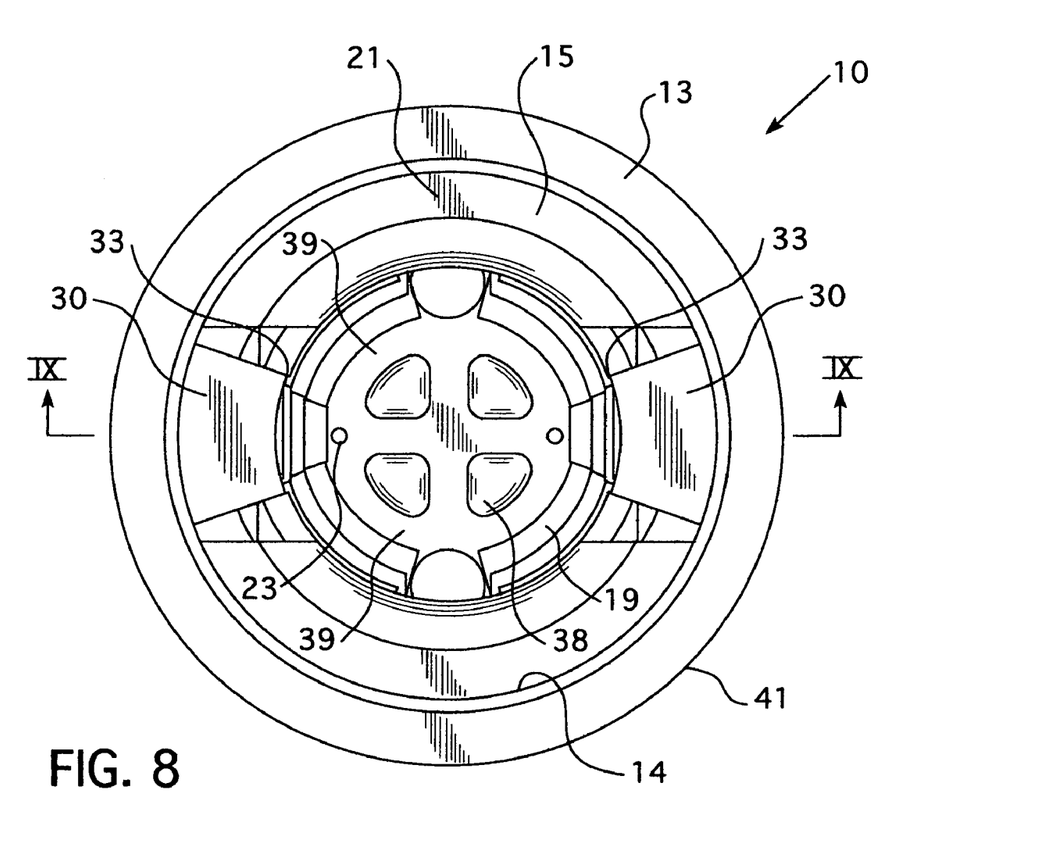
FIG. 8 is a top view of the apparatus shown in FIG. 7.
Figure 9:
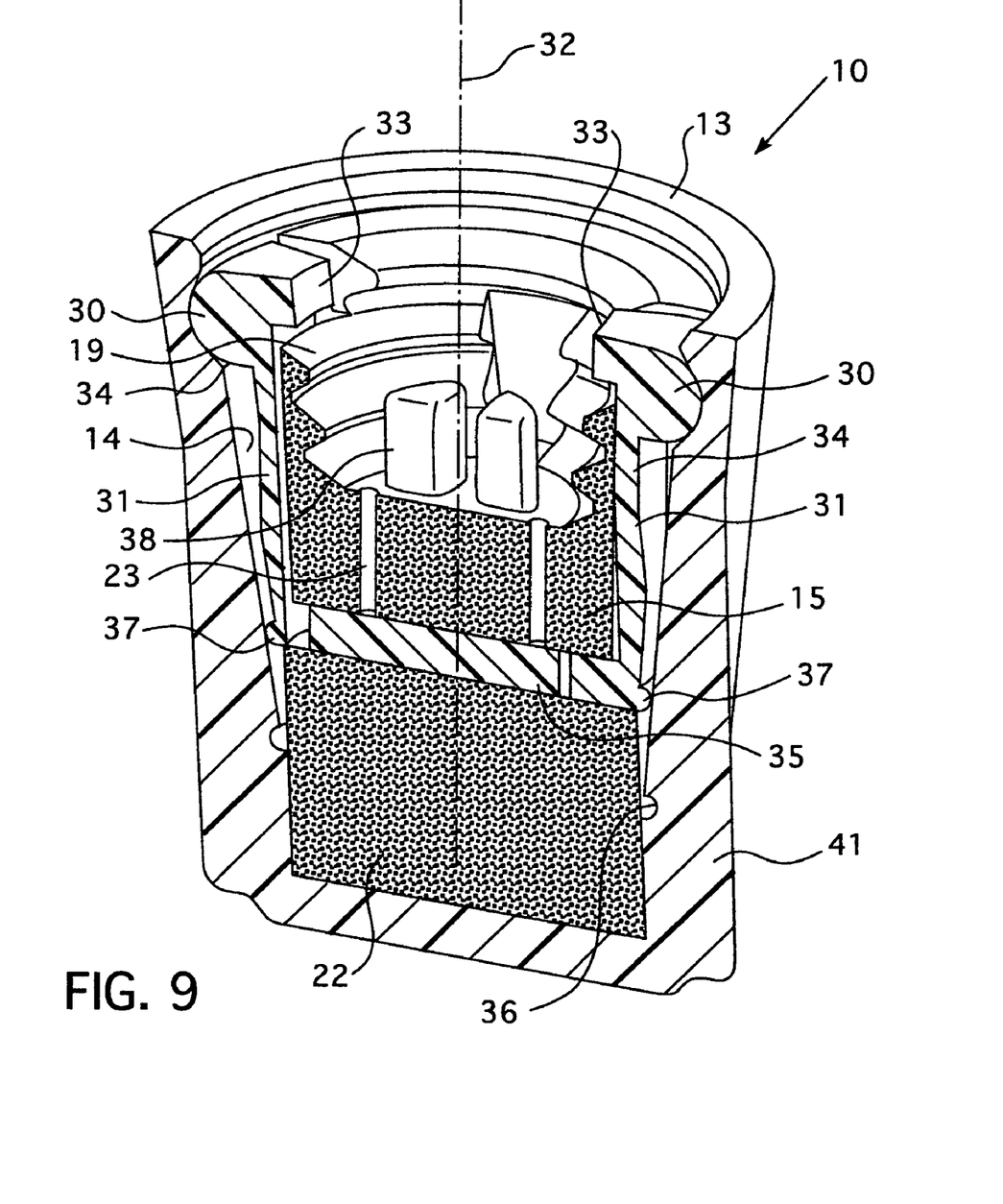
FIG. 9 is a perspective view in vertical mid cross section of the apparatus shown in FIG. 8 as seen along section line IX-IX.
Figure 10:
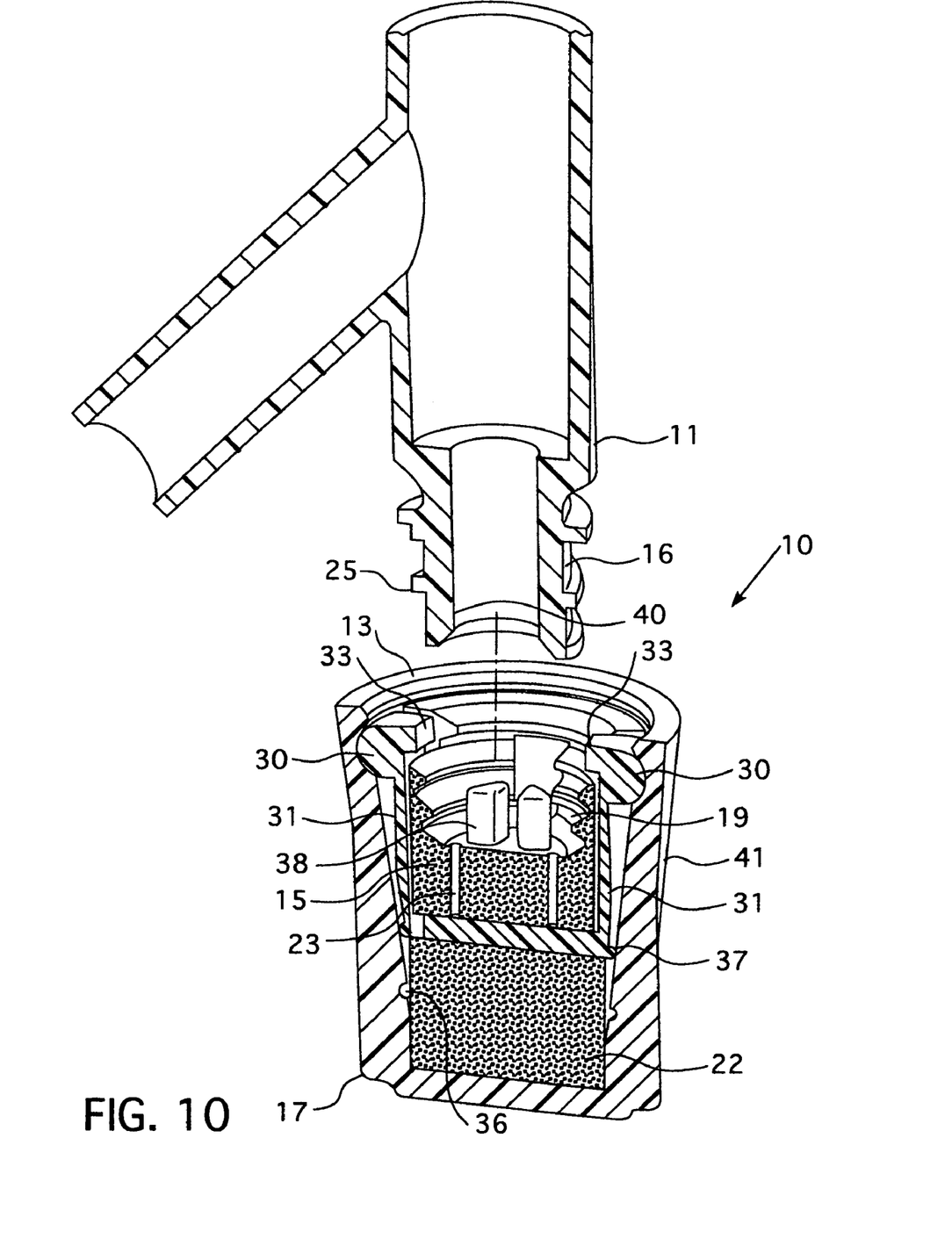
FIG. 10 is a perspective view in vertical mid cross section illustrating the apparatus shown in FIG. 9, together with a female medical line port, also shown in vertical mid cross section, just prior to insertion into the apparatus of the present invention.

Referring first to the embodiment illustrated in FIGS. 1 through 6, the apparatus 10 of the present invention is provided for sterilizing tubular medical line port (IV port) 11, as shown in FIGS. 5 and 6. In FIG. 1, the mouth of apparatus 10 is sealed off with peel-off cover seal 9. The apparatus 10 is comprised of a cap 12 having an upper open distal end 13 with a cavity 14 therein which is dimensioned to receive outer disinfectant-impregnated scrubbing member 15 and the medical line port 11 therein for sterilization. Outer disinfectant-impregnated scrubbing member 15 is coaxially received in cavity 14 and has a socket 19 therein dimensioned for engaging exterior side surfaces 16 of tubular medical line port 11 when inserted into the cavity 14 and scrubbing member 15. Scrubbing of the exterior surfaces 16 is accomplished by rotating the cap 12 by grasping the rib protrusions 17 in one hand while holding the female medical line port 11 in the other hand. Outer scrubbing member 15 consists of a pliable or yieldable plastic material.

The outer scrubbing member 15 is axially displacable downwardly in the cavity 14 by insertion of the medical line port 11 therein from an upper position illustrated in FIGS. 2 through 5 to a lower position as illustrated in FIG. 6 where it is retained to thereby indicate that the apparatus has been used and should not thereafter be reused. To provide clear indication that the apparatus 10 should not be reused, annular indicating surface 18 is provided and is exposed only after downward displacement of the outer scrubbing member 15 to the lower position illustrated in FIG. 6. The indicating surface 18 should preferably be identified by a bright color, such as red or blaze orange, to indicate to potential users that the device has been already used and should not be reused.

An annular inwardly extending protrusion 20 is provided in cavity 14 and is positioned for retaining outer scrubbing element 15 in the lower position illustrated in FIG. 6 by engaging upper surface 21 of outer scrubbing element 15 after outer scrubbing member 15 has been displaced downwardly beyond the protrusion 20 as illustrated in FIG. 6.

The sponge 22 is saturated with disinfectant fluid, such as an alcohol solution, and is positioned under outer scrubbing member 15 whereby sponge 22 is compressed to expel sterilizing fluid therefrom to the interior of outer scrubbing member 15 when displaced to the lower position illustrated in FIG. 6. Flow of the sterilization fluid from sponge 22 to the internal parts of outer scrubbing member 15 is facilitated by the passages 23.

The socket 19 of outer scrubbing member 15 is provided with female threads 24 to threadably receive and mate the male threads 25 of medical line port 11.

The internal cavity wall 26 of cap 12 is frusto-conical and tapers inwardly from the top 13 to the bottom 27 whereby outer scrubbing member 15 is squeezed radially inward upon displacement from the upper position shown in FIGS. 2 through 5 to the lower position shown in FIG. 6 when engaged and pushed by medical line port 11. This causes the application of radially inward applied pressure of the outer scrubbing member 15 for scrubbing engagement with the exterior surfaces 16 of tubular medical line port 11.

Turning next to the embodiment illustrated in FIGS. 7 through 12, like elements are indicated with the same reference numerals. This embodiment illustrates the previous embodiment with the inclusion of a reuse prevention insert so that the apparatus 10 of the present invention after initial use cannot be reused.

In this embodiment, reuse prevention insert 30 is positioned in cavity 14 and displacable with or moves with outer scrubbing member 15. Reuse prevention insert 30 is provided with two legs 31 (however, more legs than two may be provided) which are annularly disposed on and about the frusto-conical wall 26 and they are generally aligned with the central axis 32 of frusto-conical wall 26. Inwardly protruding teeth 33 protrude from upper ends 34 of legs 31. Legs 31 are in turn secured to bottom cross member 35 so that the reuse prevention insert moves with or is displaced downwardly with outer scrubbing member 15 when displaced from the upper position shown in FIGS. 7 through 10 to the lower position illustrated in FIGS. 11 and 12.

Figure 11:
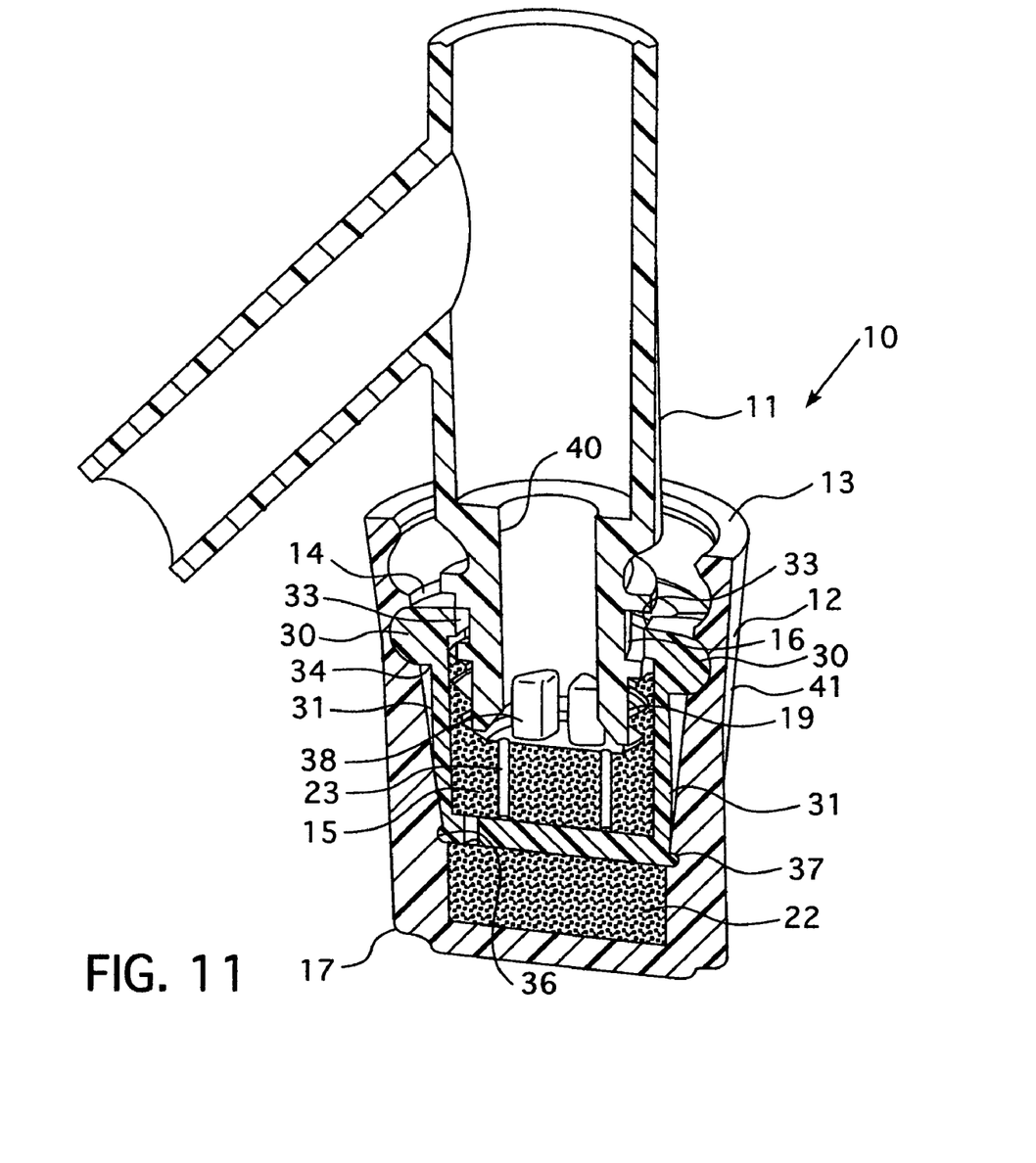
FIG. 11 is a perspective view in vertical mid cross section of the combination of elements shown in FIG. 10 after complete insertion of the female medical line port into the scrubbing apparatus of the present invention for sterilization.

Thus, when the outer scrubbing element 15, together with reuse prevention insert 30, is moved to the lower position illustrated in FIG. 11, the combination is there retained by the annular detent groove 36 in wall 26 which engages and receives corresponding annular rib 37 therein to retain the combination at the lower position illustrated in FIG. 11, in the same manner as with the first embodiment illustrated in FIGS. 1 through 6.

The wall 38 of cap 12 is comprised of a flexible plastic material so that when the reuse prevention insert 30 is moved downwardly within cavity 14 from its initial position as shown in FIGS. 7 through 10, the flexible walls 41 bias and compress the teeth 33 inwardly against the exterior surfaces 16 of tubular medical line port 11. After the surfaces 16 of port 11 are scrubbed clean by rotation of cap 12, the tubular medical line port 11 may then be unthreaded from the cap 12 under the radial inward compression of opposed teeth 33. Additional inward bias of teeth 33 may also be provided by the fact that insert 30 is also made of a compressible and flexible plastic material.

Figure 12:
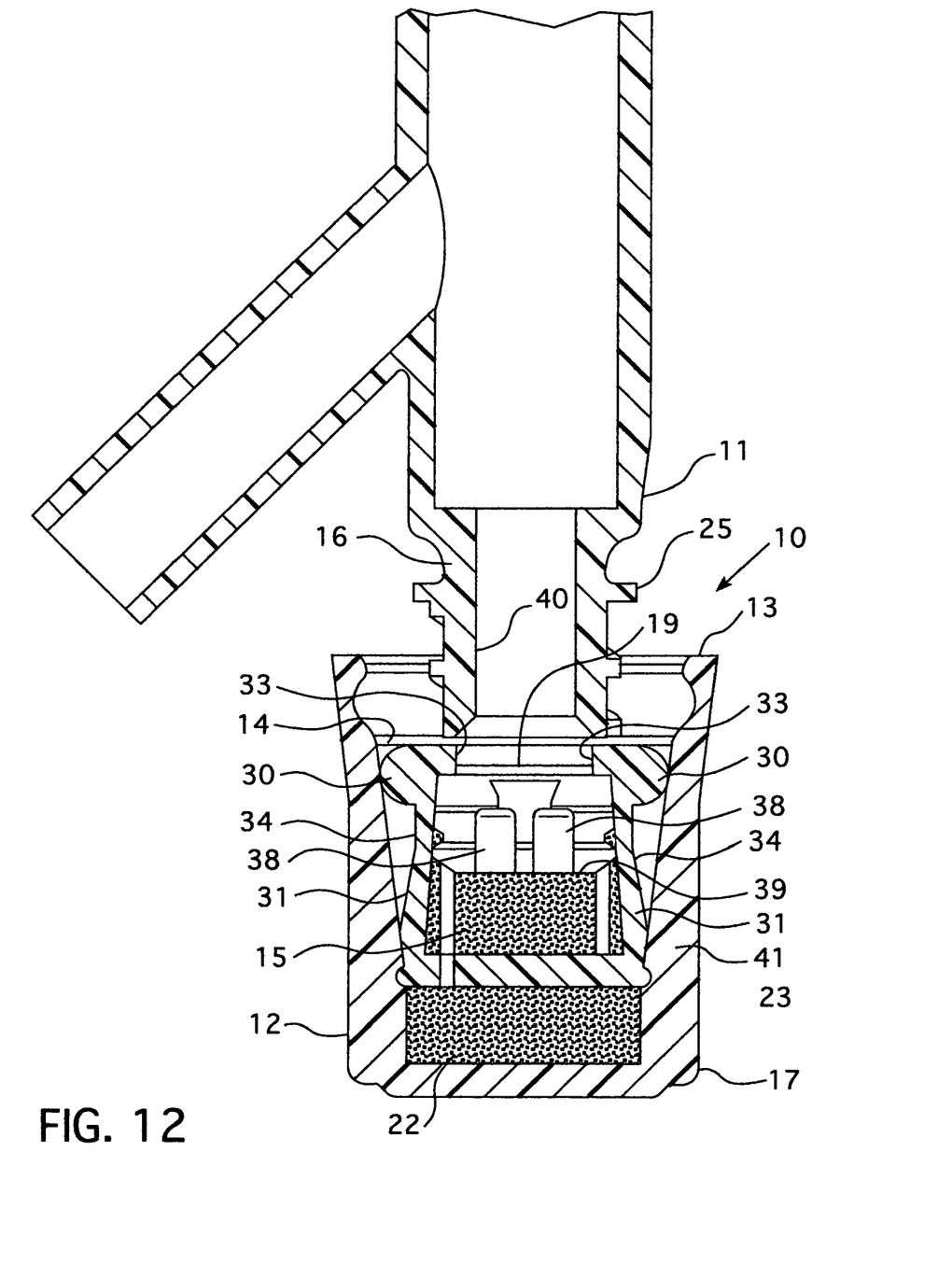
FIG. 12 is a view in front elevation of the combination illustrated in FIGS. 10 and 11 as shown in vertical mid cross section after removal of the female medical line port from the scrubbing apparatus of the present invention as illustrated in FIG. 1, illustrating how the female medical line port is prevented from reentry into the apparatus of the present invention after an initial use.

Once the female medical line port 11 has been threadably disengaged from socket 19 of apparatus 10 as illustrated in FIG. 12, the inwardly protruding teeth 33 under radial inward bias are forced yet further inward whereby they block the reentry of the port 11 into the outer scrubbing member 15 as illustrated in the figure, thereby preventing future use of the apparatus.

All embodiments are also illustrated with an inner scrubbing member 38 which extends axially upward from the bottom 39 of socket 19 of outer scrubbing element 15 for scrubbing the hollow interior 40 of tubular medical line connector 11 for sterilization.

We claim:

1. An apparatus for sterilizing a tubular medical line port, comprising:
    a cap having an open distal tubular end with a cavity therein dimensioned to receive said medical line port, an outer disinfectant-impregnated scrubbing member coaxially received in said cavity and dimensioned for engaging exterior side surfaces of said tubular medical line port when inserted into said cavity for thereby scrubbing said exterior surfaces with said member by rotating said cap;
    said outer scrubbing member axially displacable downwardly in said cavity by insertion of said medical line port therein from an upper position prior to use to a lower position where said outer scrubbing member is there retained to thereby indicate that the apparatus has been used and should not therefore be reused;
    a colored indicating surface in said cavity which is exposed only after downward displacement of said outer scrubbing member and provides a distinctive contrast to adjacent upper surfaces.

2. The apparatus of claim 1, including a compressible sponge saturated with disinfectant fluid and positioned under said outer scrubbing member whereby said sponge is compressed to expel said fluid therefrom to said outer scrubbing member when displaced to said lower position.

3. The apparatus of claim 1, including an annular inwardly extending protrusion in said cavity positioned for retaining said outer scrubbing member in said lower position by engaging an upper surface of said outer scrubbing member after said outer scrubbing member is displaced downwardly beyond said protrusion.

4. The apparatus of claim 1, wherein said outer scrubbing member includes female threads to threadably receive and mate male threads on said medical line port.

5. The apparatus of claim 1, wherein said cavity has a frusto-conical wall which tapers inwardly from top to bottom whereby said outer scrubbing member is squeezed radially inward upon displacement to said lower position for pressure scrubbing engagement with said medical line port.

6. The apparatus of claim 5, including a reuse prevention insert in said cavity and displacable with said outer scrubbing member, said insert having inwardly protruding and inwardly biased lips which prevent re-access of a medical line port into said cavity after removal of said medical line port from said outer scrubbing member under the biased inward engagement of said lips.

7. The apparatus of claim 6, said reuse prevention insert including multiple legs annularly disposed on and about said frusto-conical wall and generally aligned with the central axis of said wall, said lips protruding from upper ends of said legs.

8. The apparatus of claim 7, said lips inwardly biased by said frusto-conical wall.

9. The apparatus of claim 7, said wall comprised of flexible material.

10. The apparatus of claim 1, said outer scrubbing member including an inner scrubbing member extending axially upward from a bottom of said outer scrubbing element.

11. An apparatus for sterilizing a tubular medical line port comprising:
    a cap having an open distal end with a cavity therein coaxially receiving an outer disinfectant-impregnated scrubbing member having a socket therein dimensioned for receiving and engaging exterior side surfaces of said tubular medical line port when inserted into said socket for thereby scrubbing said exterior surfaces with said member by rotating said cap;
    a reuse prevention insert in said cavity retaining inwardly protruding teeth which are biased to partially close of said socket when a medical line port is removed from said socket whereby re-access of a medical line port into said socket is prevented.

* * * * *